(12) United States Patent
Cheng et al.

(10) Patent No.: US 9,185,928 B2
(45) Date of Patent: Nov. 17, 2015

(54) MESOPOROUS SILICA NANOPARTICLES FOR OIL ABSORPTION

(71) Applicant: NATIONAL HEALTH RESEARCH INSTITUTES, Miaoli County (TW)

(72) Inventors: Shin-Hsun Cheng, Miaoli County (TW); Wei-Neng Liao, Miaoli County (TW); Chung-Shi Yang, Miaoli County (TW); Leu-Wei Lo, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 35 days.

(21) Appl. No.: 14/135,600

(22) Filed: Dec. 20, 2013

(65) Prior Publication Data

US 2014/0178505 A1    Jun. 26, 2014

Related U.S. Application Data

(60) Provisional application No. 61/740,768, filed on Dec. 21, 2012.

(51) Int. Cl.
*A61K 33/00* (2006.01)
*A23L 1/304* (2006.01)
*A61K 9/51* (2006.01)

(52) U.S. Cl.
CPC . *A23L 1/304* (2013.01); *A61K 9/51* (2013.01); *A23V 2002/00* (2013.01)

(58) Field of Classification Search
CPC .......... A61K 33/00; A61K 9/51; A23L 1/304; A23V 2002/00; A23V 2200/25; A23V 2200/32; A23V 2200/332; A23V 2250/1628
See application file for complete search history.

(56) References Cited

U.S. PATENT DOCUMENTS

| 6,756,364 | B2 | 6/2004 | Barbier et al. |
| 7,049,345 | B2 * | 5/2006 | Holmes-Farley .......... 424/78.27 |
| 2008/0038318 | A1 | 2/2008 | Tuomasjukka |
| 2010/0010465 | A1 | 1/2010 | Winqvist et al. |

FOREIGN PATENT DOCUMENTS

| EP | 2 016 946 B1 | 1/2009 |
| WO | WO 9936075 A1 * | 7/1999 |

OTHER PUBLICATIONS

Radislav Filipović, Dragica Lazić, Mitar Peruš ić and Ivan Stijepović, "Oil absorption in mesoporous silica particles", Processing and Application of Ceramics 4 [4] (2010) 265-269.*
Asep Bayu Dani Nandiyanto, Soon-Gil Kim, Ferry Iskandar, Kikuo Okuyama, Synthesis of spherical mesoporous silica nanoparticles with nanometer-size controllable pores and outer diameters, Microporous and Mesoporous Materials 120 (2009) 447-453.
Shengyang Tao, Yuchao Wang and Yonglin An, Superwetting monolithic SiO2 with hierarchical structure for oil removal J. Mater. Chem., 2011, 21, 11901-11907.

* cited by examiner

*Primary Examiner* — John Pak
*Assistant Examiner* — Nathan W Schlientz
(74) *Attorney, Agent, or Firm* — Hsiu-Ming Saunders; Intellectual Property Connections, Inc.

(57) ABSTRACT

A method for prevention and/or treatment of steatorrhea in a subject is disclosed. The method comprises administering to the subject a composition comprising mesoporous silica nanoparticles (MSNs) in an amount effective for prevention and/or treatment of steatorrhea in the subject

19 Claims, 4 Drawing Sheets

FIG 2
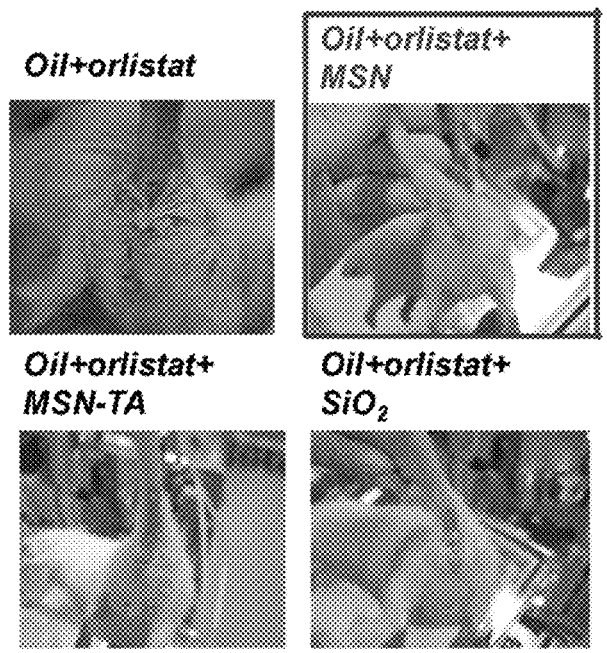
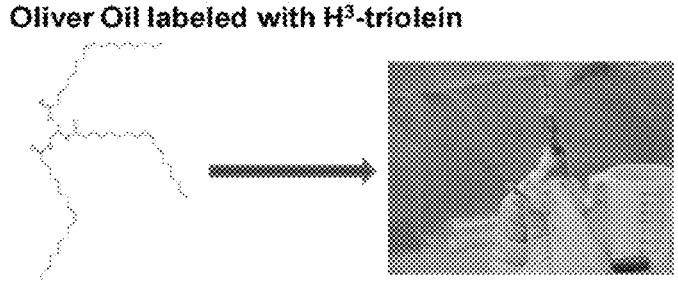
FIG. 5A
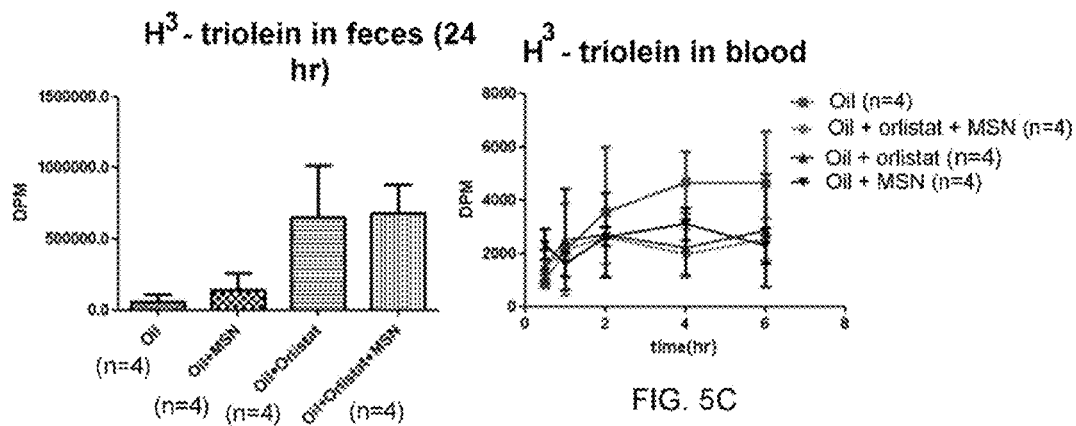
FIG. 5B
FIG. 5C

FIG 3

|  | Mesoporous silica nanoparticles | Prior Art 1: Gastrointestinal side effects of orlistat may be prevented by concomitant prescription of natural fiber (International Jouranl of Obesity (2001), 25, 1095-1099) | Prior Art 2: Method of reducing gastrointestinal side effect associated with orlistat treatment (ref. US Patent No. 6756364 B2) |
|---|---|---|---|
| Components | $SiO_2$ | Psyllium mucilloid Plant fiber | Cholestyramine, colestipol, Diethylaminoethylcellulose Starch derivatives |
| Dosage | Orlistat(25mg): MSN(60mg)= 1:2.4(rat) | Orlistat(120mg): Psyllium mucilloid(6g) =1:50(human) | Orlistat(120mg) Cholestyramine, Colestipol:4000mg/ Diethylaminoethylcellulose :240mg /Starch derivatives: 740mg |
| Drug Ratio (Orlistat : additive materials) | 1:18.5 (human) | 1:50 (human) | 1:42 (human) |
| Side effect |  | High dose: the risk of bowel obstruction | Colestipol can induce Gastrointestinal disturbances, especially (mild, occasionally severe) constipation |

FIG 4

|  | Oil + orlistat<br>Rat n= 6 | Oil + orlistat +<br>MSN<br>Rat n=8 | Oil + orlistat +<br>MSN-TA<br>Rat n=6 | Oil + orlistat +<br>SiO2<br>Rat n=6 |
|---|---|---|---|---|
| Dose | Oil:450mg<br><br>Orlistat:25mg/1 mL water | Oil:450mg<br><br>Orlistat:25mg/ 1mL water<br><br>MSN:60mg/ml | Oil:450mg<br><br>Orlistat:25mg/1 mL water<br><br>MSN-TA:60mg/ml | Oil:450mg<br><br>Orlistat:25mg/ 1mL water<br><br>$SiO_2$:60mg/ml |
| Method | Oral | Oral (Orlistat and MSN mixture) | Oral (Orlistat and MSN-TA mixture) | Oral (Orlistat and $SiO_2$ mixture) |
| Efficacy (Eliminate ratio of Side Effect) Time: 24hr | 0%<br>(n=0/6) | 100%<br>(8/8) | 17%<br>(1/6) | 0%<br>(0/6) |

MESOPOROUS SILICA NANOPARTICLES FOR OIL ABSORPTION

REFERENCE TO RELATED APPLICATION

The present application claims the priority to U.S. Provisional Application Ser. No. 61/740,768, filed Dec. 21, 2012, which is herein incorporated by reference in its entirety.

FIELD OF THE INVENTION

The present invention relates to pharmaceutical combinations, compositions and methods for treating obesity and steatorrhea.

BACKGROUND OF THE INVENTION

Orlistat (also known as tetrahydrolipstatin and sold under the brand name XENICAL™) is a potent inhibitor of gastrointestinal lipases, i.e. lipases that are responsible for breaking down ingested fat (gastric lipase, carboxylester lipase, pancreatic lipase). As a consequence of this, unabsorbed fat is excreted in the feces. Pancreatic lipase is the key enzyme for the hydrolysis of dietary triglycerides. Triglycerides that have escaped hydrolysis are not absorbed in the intestine. Pharmacological studies with human patients have demonstrated that potent inhibition of fat absorption and medically relevant reduction of body weight were achieved using lipase inhibitors. However, in a subgroup of the patients unpleasant gastrointestinal side effects such as oily spotting, fatty/oily stool, fecal urgency, increased defecation and fecal incontinence were observed. Accordingly, there is a need in the art for compositions that minimize or suppress the side effects caused by inhibitors of digestive lipases.

SUMMARY OF THE INVENTION

In one aspect, the invention relates to a method for prevention and/or treatment of steatorrhea in a subject, comprising administering to the subject a composition comprising mesoporous silica nanoparticles (MSNs) in an amount effective for prevention and/or treatment of steatorrhea in the subject.

In one embodiment of the invention, the steatorrhea is caused by a lipase inhibitor treatment received by the subject.

In another embodiment of the invention, the composition comprising the MSNs is administered to the subject concurrently with the lipase inhibitor treatment.

In another embodiment of the invention, the lipase inhibitor is orlistat.

In another embodiment of the invention, the composition comprises the MSNs and the lipase inhibitor.

In another embodiment of the invention, the administering step is performed after a meal.

In another embodiment of the invention, the composition is a water suspension.

In another embodiment of the invention, the MSNs are unmodified with any functional group.

In another embodiment of the invention, me MSNs are unmodified with tertiary amine groups.

In another embodiment of the invention, the composition does not comprise silica nanoparticles that are not in mesoporous form.

In another aspect, the invention relates to a method for causing a liquid lipid to gel and/or solidify, comprising the step of exposing the liquid lipid to, or causing the liquid lipid to contact with, a composition comprising mesoporous silica nanoparticles (MSNs) in an amount effective for causing the liquid lipid to gel and/or solidify. The lipid is animal oil, vegetable oil, or crude oil.

In one embodiment of the invention, the liquid lipid is a dietary lipid and the step of exposing the liquid lipid to, or causing the liquid lipid to contact with, the MSNs occurs inside intestines of a subject.

In another embodiment of the invention, the subject is suffered from steatorrhea.

In another embodiment of the invention, the subject receives a lipase inhibitor treatment and the steatorrhea is caused by the lipase inhibitor treatment.

In another embodiment of the invention, the step is performed concurrently with the lipase inhibitor treatment in the subject.

In another embodiment of the invention, the composition comprising the MSNs and a lipase inhibitor.

In another embodiment of the invention, the dietary lipid is at least one selected from the group consisting of triglycerides, fats, oils.

In another embodiment of the invention, the composition is a dietary product containing the MSNs as a food additive.

In another embodiment of the invention, the dietary product is a food product or a drink product.

In another embodiment of the invention, the percentage weight ratio of the MSNs in the composition is one selected from the group consisting of 10% (w/w) to 50% (w/w) and 5% (w/w) to 30% (w/w).

Further in another aspect, the invention relates to a method of causing a liquid dietary lipid to gel and/or solidify for reducing intestinal absorption of the dietary lipid, comprising the step of administering to a subject a composition comprising mesoporous silica nanoparticles (MSNs) in an amount effective for causing the liquid dietary lipid to gel and/or solidify for reducing intestinal absorption of the dietary lipid in the subject.

The invention further relates to a method for reducing intestinal absorption of the dietary lipid comprising administering to a subject in need thereof a composition comprising an effective amount of mesoporous silica nanoparticles (MSNs).

In one embodiment of the invention, the composition does not comprise any other therapeutic compound except the MSNs. Alternatively, the composition may comprise MSNs and a lipase inhibitor such as orlistat but not any other drugs. That is, any other drugs or therapeutic compounds are excluded from the composition except the MSNs and a lipase inhibitor such as orlistat.

The dietary lipid may be selected from the group consisting of canola oil, corn oil, cottonseed oil, olive oil, safflower oil, soybean oil, sunflower oil, walnut oil and sesame oil.

In another embodiment of the invention, the dietary lipid may be a fat selected from the group consisting of butter, milk fat, beef fat, chicken fat, pork fat, margarine, shortening, and partially hydrogenated oil.

In another embodiment of the invention, the aforementioned MSNs are positively charged mesoporous silica nanoparticles (MSNs-TA), which comprises: a) a silica matrix, the entire substance of which comprises a plurality of silanol (Si—OH) and quaternary ammonium functional groups; and b) an array of pores and/or nanochannels in the matrix, each pore and/or nanochannel having a surface lining the wail thereof; wherein the surface lining the wall of each pore and/or nanochannel comprises a plurality of silanol (Si—OH) and quaternary ammonium functional groups, as disclosed in U.S. Pat. No. 8,252,337, which is herein incorporated by reference in its entirety. In another embodiment of the invention, the aforementioned MSNs is without any surface modification.

In another aspect, the invention relates to a method for curing oil, comprising exposing oil to a composition comprising an effective amount of MSNs; or causing oil to be in contact with a composition comprising an effective amount of MSNs, and thereby curing the oil.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 2 shows the photographs taken 24 hrs after the rats were administered with orlistat with or without the nanoparticle samples.

FIG. 3 is a chart showing comparisons of the amounts of orlistat and anti-stearorrhea drugs.

FIG. 4 shows in vivo efficacy of MSNs, SiO2 nanoparticles, and MSN with quaternary ammonium functional groups (MSN-TA) on orlistat-induced steatorrhea. Mice were treated with drugs 30 minutes after oil intakes.

FIGS. 5A-C show isotope labeling of oil and oil administration to a rat by oral gavage (FIG. 5A) to prove that the MSNs does not affect the function of orlistat by measuring tritium in stools (FIG. 5B) and blood (FIG. 5C).

DETAILED DESCRIPTION OF THE INVENTION

Figure 1A:
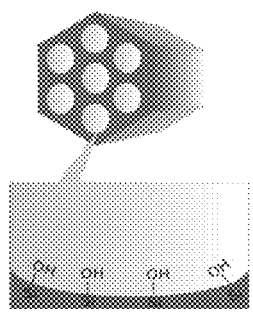
FIG. 1A is a schematic drawing showing a mesoporous silica nanoparticle (MSN).

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Curing is a term in polymer chemistry and process engineering that refers to the toughening or hardening of a polymer material by cross-linking of polymer chains, brought about by chemical additives, ultraviolet radiation, electron beam or heat.

An oil is any neutral chemical substance that is a viscous liquid at ambient temperatures, is immiscible with water but soluble in alcohols or ethers. Oils have a high carbon and hydrogen content and are usually flammable and slippery (nonpolar). Oils may be animal, vegetable, or petrochemical in origin, volatile or non-volatile.

Dietary lipids include, e.g., triglycerides, fats, oils. Steatorrhea (oily, loose stools) is the presence of excess fat in the stools.

As used herein, when a number or a range is recited, ordinary skill in the art understand it intends to encompass an appropriate, reasonable range for the particular field related to the invention.

By ranging from 10% (w/w) to 50% (w/w) it meant that all integer unit amounts within the range are specifically disclosed as part of the invention. Thus, 10% (w/w), 11% (w/w), 12% (w/w) . . . 47% (w/w), 48% (w/w), 49% (w/w) and 50% (w/w) unit amounts are included as embodiments of this invention.

By ranging from 5% (w/w) to 30% (w/w) it meant that all integer unit amounts within the range are specifically disclosed as part of the invention. Thus, 5% (w/w), 6% (w/w), 7% (w/w) ... 27% (w/w), 28% (w/w), 29% (w/w) and 30% (w/w) unit amounts are included as embodiments of this invention.

As used herein, "MSN-TA" refers to a mesoporous silica nanoparticle that has been modified by trimethylammonium (TA) functional groups. The TA functional groups are incorporated into the matrix (and/or framework) of the MSN via a co-condensation method. The MSN-TA is a positively charged mesoporous silica nanoparticle (MSN) composed of a silica matrix and an array of pores and/or nanochannels in the matrix. Each pore and/or nanochannel has a surface lining the wall of the pore and/or nanochannel. The matrix substance, all the surfaces and inside the pores comprise a plurality of quaternary ammonium and silanol (Si—OH) functional groups. The surface lining the wall of the pore comprises a plurality of silanol (Si—OH) and quaternary ammonium functional groups. The entire matrix, all the surfaces, and the surfaces lining the walls of the pores all comprise quaternary ammonium functional groups.

The terms "orlistat" and "tetrahydrolipstatin" are interchangeable.

The term "treating" or "treatment" refers to administration of an effective amount of the compound to a subject in need thereof with the purpose of cure, alleviate, reducing, relieve, remedy, ameliorate, or prevent the disease, the symptoms of it, or the predisposition towards it. Such a subject can be identified by a health care professional based on results from any suitable diagnostic method.

The term "an effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by a calculation from the following formula:

$$HED = \text{animal dose in mg/kg} \times (\text{animal weight in kg/human weight in kg})^{0.33}.$$

The average body weight of rats is about 300 gram. In FIG. 2, the amount of MSNs administered to the rats was about 198 mg/kg. Thus, as a starting point, a therapeutic amount of MSNs for a human being may be calculated as follows:

$$HED = 198 \text{ mg/kg} \times (0.3 \text{ kg/human weight in kg})^{0.33}.$$

The invention relates to mesoporous silica nanoparticles (MSNs) as a oil curing agent to reduce the side effect oily stool induced by a lipase inhibitor such as orlistat.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

In vitro Study

Oil curing evidence: Oil and Oil with MSN, SiO2, MSN-TA in tube test

The interactions of oil and the nanoparticle sample, mesoporous silica nanoparticles (MSNs), silica nanoparticles or MSNs-TA, in the presence and absence of water were examined by the oil curing test. The sample MSNs, Silica NPs, MSNs-TA (16 mg each) in powder form were respectively added to the olive oil (120 mg) inside the microcentrifuge tubes. In parallel, the nanoparticle samples (16 mg each) were suspended in water to form water suspensions, and the water suspensions were added respectively into the olive oil (120 mg) insider the tubes. The oil and the nanoparticle samples were mixed by shaking for 30 s and let the mixture aged for 6 hr and the oil curing state was examined.

In vivo Study 1

Rats fed with a high fat diet followed by orlistat treatment had oily sloppy loose stools that contaminated their fur around the anus. To investigate the reduction of orlistat side effects by the nanoparticle samples, MSN, MSN-TA and silica nanoparticles, an in vivo study was conducted. Orlistat at a concentration of 25 mg/ml and the nanoparticle samples each at a concentration of 60 mg/ml were used in the study. Rats were fed with olive oil (450 mg) first by oral gavage, then oristat or the combination of oristat plus a nanoparticle sample suspended in water was fed into the rats 30 minutes after the oil administration by oral gavage. Rats were observed for loose stools after 24 hrs. In this study, the SD rats were divided into 4 groups. Rats in the first group were fed with orlistat (n=6); rats in the second group were fed with orlistat (25 mg/ml)+MSNs (n=8), rats in the third group were fed with orlistat+MSNs-TA (n=6); rats in the fourth group were fed with orlistat+SiO2 (n=6) 30 minutes after the olive oil administration by oral gavage.

In vivo Study 2

The question of whether MSNs would affect the activity of orlistat in vivo was investigated. In this study, olive oil was labeled with $^3$H-triolein (as the tracer) and the excretion of oil was quantified by a beta counter. Orlistat at a concentration of 25 mg/ml and the nanoparticle samples each at a concentration of 60 mg/ml were used.

The SD rats were divided into 4 groups. Rate in the first group were fed with oil only (n=4); rats in the second group were fed with oil+MSNs (n=4), rats in the third group were fed with oil+orlistat (n=4); rats in the fourth group were fed with oil+orlistat+MSNs (n=4) 30 minutes after the olive oil administration by oral gavage. Orlistat and MSNs were mixed and suspended in water to form a suspension. In practice, rats were fed with olive oil (450 mg) labeled with $^3$H-triolein (25 μl, 3 μCi) first by oral gavage, then oristat or the combination of oristat plus a nanoparticle sample suspended in water was fed into the rats 30 minutes after the oil gavage. The feces were collected after 24 hr, and blood collected after 30 min, 1 hr, 2 hr, 4 hr, and 6 hr. The feces and blood were respectively mixed with ULTIMA GOLD™ Safer LSC Cocktails, and then counted for beta emission after digestion by acid and hydrogen peroxide in 50° C. The counts of the feces and blood were obtained by measuring the quantitative amount of $^3$H-triolein in the feces and blood to determine the drug activity of orlistat in the presence and absence of MSNs.

Results

Figure 1B:
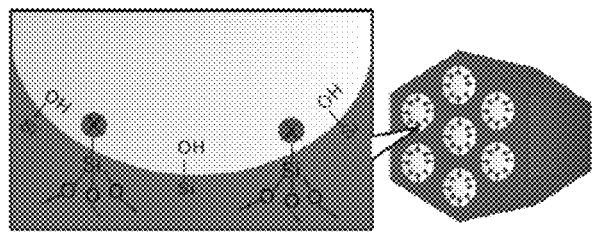
FIG. 1B is a schematic drawing showing a mesoporous silica nanoparticle-trimethylammonium (MSN-TA). The circled X represents a "trimethylammonium" functional group.
Figure 1C:
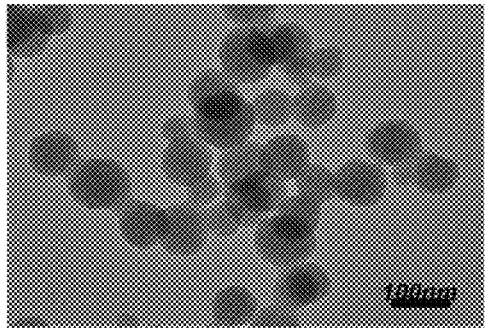
FIG. 1C shows MSNs under TEM.
Figure 1D:
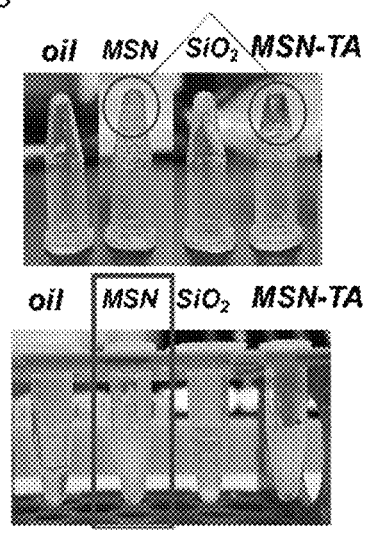
FIG. 1D shows liquid oil congealed (solidified) in vitro after addition of a powder form of MSNs, SiO2 nanoparticles, or MSN with quaternary ammonium functional groups (MSN-TA) (upper panel), but not after addition of water suspensions of MSNs, SiO2 nanoparticles, or MSN with quaternary ammonium functional groups (MSN-TA) (lower panel) into the olive oil inside the tubes.

Reduce side effect of orlistat. FIGS. 1A-B illustrate the structure of a MSN and a MSN-TA. FIG. 1C shows MSNs under TEM. Material characteristics of mesoporous silica NPs are as follows. TEM size: 102.1±16.17 nm; DLS: 132.8±30.24 nm; Surface area: 1027.5 m²/g; Pore size: 2.56 nm. FIG. 1D shows liquid oil congealed (solidified) in vitro after the powder forms of MSNs, SiO2 nanoparticles, or MSN with quaternary ammonium functional groups (MSN-TA) were added into the oil inside the tube (upper panel). Oil solid pieces/chunks (gel-like) occurred after the MSNs in powder form were directly added into the liquid oil. The two circles show the solidified oil adhering to the wall at the bottom of the tube, a curing phenomena. The liquid oil did not congeal after the water suspensions of MSNs, SiO2 nanoparticles, or MSN with quaternary ammonium functional groups (MSN-TA) were added into the olive oil inside the tube (lower panel). The box shows the most uniform of the mixture formed after the water suspension form of MSN was added into the oil insider the tube.

FIG. 2 shows the in vivo effects of MSNs, SiO2 nanoparticles, and MSN with quaternary ammonium functional groups (MSN-TA) on orlistat-induced steatorrhea (oily, loose stools with excessive flatus due to unabsorbed fats reaching the lame intestine). Rats administered with the combination of orlistat and MSN showed no significant side effects of orlistat.

FIG. 3 is a chart showing comparisons of the amounts of orlistat and anti-stearorrhea drugs.

FIG. 4 shows in vivo efficacy of MSNs, SrO2 nanoparticles, and MSN with quaternary ammonium functional groups (MSN-TA) on orlistat-induced steatorrhea. Mice were treated with the drugs 30 minutes after the oil intake. The eliminate ratio was defined as the number of rats who had no oily feces divided by the number of total rats in the experimental group. The ratios 8/8, 1/6, 0/6 stand for that 8 out of 8, 1 out of 6, 0 out of 6 had no oily stool, respectively.

FIGS. 5A-C show the use of isotope labeling of oil (FIG. 5A) to prove that the MSNs does not affect the function of orlistat by measuring the tritium in faces (FIG. 5B) and blood (FIG. 5C).

The experimental results indicated that Mesoporous silica nanoparticles (MSNs) can be a oil curing agent to reduce side effect of orlistat Advantages of MSNs in the Medical Market The major advantage of using MSNs in the medical market is the safety. Nature silica materials have been approved by FDA as drug and food additives. Another advantage concerns the manufacture. MSNs' origin of production is easily available and inexpensive. Thus, they have competitiveness potential in the market. MSNs can be used as oral drug carrier and to protect some drugs from digestion by stomach acid. MSNs have large surface area to absorb hydrophobic compounds like fat, and bile salt in their channels and prevent enzyme interaction. Thus, they can be used as an absorbed tracer or a nutrients carrier (like hydrophobic vitamins).

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for reducing the incidence of and/or treating steatorrhea, comprising:
   administering to a subject in need thereof a composition comprising an effective amount of mesoporous silica nanoparticles (MSNs), and thereby reducing the incidence of and/or treating steatorrhea in the subject.

2. The method of claim 1, wherein the steatorrhea is caused by a lipase inhibitor treatment in the subject.

3. The method of claim 2, wherein the composition comprising the MSNs is administered to the subject concurrently with the lipase inhibitor treatment.

4. The method of claim 2, wherein the lipase inhibitor is orlistat.

5. The method of claim 2, wherein the composition comprises the MSNs and the lipase inhibitor.

6. The method of claim 1, wherein the administering step is performed after a meal.

7. The method of claim 1. wherein the composition is a water suspension.

8. The method of claim 1, wherein the MSNs are unmodified with any functional group.

9. The method of claim 8, wherein the MSNs are unmodified with tertiary amine groups.

10. A method for causing a liquid lipid to gel and/or solidify, comprising the step of: exposing the liquid lipid to a composition comprising an effective amount of mesoporous silica nanoparticles (MSNs), and thereby causing the liquid lipid to gel and/or solidify, wherein the exposing step exposes a liquid dietary lipid inside intestines of a subject to the MSNs, and thereby causing the liquid lipid to gel and/or solidify inside the intestines of the subject.

11. The method of claim 10, wherein the subject is suffering from steatorrhea.

12. The method of claim 11, wherein the steatorrhea is caused by lipase inhibitor treatment in the subject.

13. The method of claim 12, wherein the exposing step is performed concurrently with the lipase inhibitor treatment in the subject.

14. The method of claim 10, wherein the composition comprises the MSNs and a lipase inhibitor.

15. The method of claim 10, wherein the liquid dietary lipid is at least one selected from the group consisting of triglycerides, fats and oils.

16. The method of claim 10, wherein the composition is a dietary product containing the MSNs as a food additive.

17. The method of claim 16, wherein the dietary product is a food product or a drink product.

18. The method of claim 16, wherein the percentage weight ratio of the MSNs in the composition is one selected from the group consisting of 10% (w/w) to 50% (w/w) and 5% (w/w) to 30% (w/w).

19. A method of causing a liquid dietary lipid to gel and/or solidify for reducing intestinal absorption of the dietary lipid, comprising the step of:
   administering to a subject in need thereof a composition comprising an effective amount of mesoporous silica nanoparticles (MSNs), and thereby causing the liquid dietary lipid to gel and/or solidify and reducing intestinal absorption of the dietary lipid in the subject.

* * * * *